United States Patent [19]

Sharpe et al.

[11] Patent Number: 5,631,017

[45] Date of Patent: *May 20, 1997

[54] TOPICAL APPLICATION OF BUSPIRONE FOR TREATMENT OF PATHOLOGICAL CONDITIONS ASSOCIATED WITH IMMUNE RESPONSES

[75] Inventors: Richard J. Sharpe, Cambridge; Kenneth A. Arndt, Newton Centre; Stephen J. Galli, Winchester, all of Mass.

[73] Assignee: Beth Israel Deaconess Medical Center, Inc., Boston, Mass.

[ * ] Notice: The term of this patent shall not extend beyond the expiration date of Pat. No. 5,484,788.

[21] Appl. No.: 37,225

[22] Filed: Mar. 26, 1993

[51] Int. Cl.$^6$ .................................................. A61F 13/00
[52] U.S. Cl. .......................... 424/449; 424/427; 424/434; 514/275
[58] Field of Search .......................... 514/275; 424/427, 424/434, 499

[56] References Cited

U.S. PATENT DOCUMENTS

| | | | |
|---|---|---|---|
| 3,717,634 | 2/1973 | Wu et al. | 514/252 |
| 3,976,776 | 8/1976 | Wu et al. | 424/251 |
| 4,182,763 | 1/1980 | Casten et al. | 514/252 |
| 4,351,939 | 9/1982 | Simms et al. | 544/230 |
| 4,417,049 | 11/1983 | Sims | 544/231 |
| 4,438,119 | 3/1984 | Allen et al. | 514/252 |
| 4,468,391 | 8/1984 | Voith | 514/221 |
| 4,515,947 | 5/1985 | Sandefur et al. | 544/295 |
| 4,620,006 | 10/1986 | Sandefur et al. | 544/402 |
| 4,634,703 | 1/1987 | Kurtz et al. | 514/252 |
| 4,636,563 | 1/1987 | Abou-Gharbia | 546/87 |
| 4,640,921 | 2/1987 | Othmer et al. | 514/252 |
| 4,687,772 | 8/1987 | Alderdice | 514/273 |
| 4,696,927 | 9/1987 | Gittos et al. | 514/228.8 |
| 4,709,027 | 11/1987 | Abou-Gharbia et al. | 544/6 |
| 4,732,984 | 3/1988 | Abou-Gharbia et al. | 544/295 |

(List continued on next page.)

FOREIGN PATENT DOCUMENTS

| | | |
|---|---|---|
| 170213 | 7/1985 | European Pat. Off. . |
| 223344 | 9/1986 | European Pat. Off. . |
| 440851 | 2/1990 | European Pat. Off. . |
| 442423 | 2/1991 | European Pat. Off. . |
| 497314 | 8/1992 | European Pat. Off. . |
| 2057845 | 6/1971 | Germany . |
| 2089341 | 6/1982 | United Kingdom . |
| 2139217 | 11/1984 | United Kingdom . |
| WO88/07529 | 10/1988 | WIPO . |
| WO92/00070 | 1/1989 | WIPO . |
| WO89/03676 | 5/1989 | WIPO . |
| WO89/04311 | 5/1989 | WIPO . |
| WO91/02497 | 3/1991 | WIPO . |
| WO91/02527 | 3/1991 | WIPO . |
| WO91/13622 | 9/1991 | WIPO . |
| WO92/09252 | 6/1992 | WIPO . |
| WO92/19226 | 11/1992 | WIPO . |
| WO93/12789 | 7/1993 | WIPO . |

OTHER PUBLICATIONS

Freire–Garabal M. et al., "Effects of Buspirone on the Immunosuppressive Response to Stress in Mice", *Arch. int. Pharmacodyn* 314, 160–168 (1991).

Allen, L.E., et al., *Arneimittel–Forsch*, vol. 24, p. 917 (1974).

Ameisen, J.C., et al., "A New Interpretation of the Involvement of Serotonin in Delayed–Type Hypersensitivity," J. Immunology, vol. 142, No.9, pp. 3171–3179 (1989).

(List continued on next page.)

Primary Examiner—Jyothsna Venkat
Attorney, Agent, or Firm—Kilpatrick & Cody, L.L.P.

[57] ABSTRACT

A method for the treatment of a cutaneous, ocular, or mucosal pathological condition which is associated with an immune response in a human or other mammal, that includes topical application of an effective amount of buspirone or a buspirone derivative or its pharmaceutically acceptable salt, optionally in a pharmaceutically-acceptable diluent or carrier for topical application.

12 Claims, 2 Drawing Sheets

U.S. PATENT DOCUMENTS

| | | |
|---|---|---|
| 4,748,240 | 5/1988 | Stack et al. .................. 544/47 |
| 4,777,173 | 10/1988 | Shrotryia et al. ............ 514/252 |
| 4,788,189 | 11/1988 | Glazer ........................... 514/221 |
| 4,810,789 | 3/1989 | Behme et al. ................. 544/230 |
| 4,812,567 | 3/1989 | Abou-Gharbia ............. 544/230 |
| 4,851,533 | 7/1989 | Abou-Gharbia ............. 544/405 |
| 4,883,875 | 11/1989 | Abou-Gharbia ............. 546/16 |
| 4,895,848 | 1/1990 | Traber et al. ................. 514/255 |
| 4,900,835 | 2/1990 | Abou-Gharbia .............. 546/272 |
| 4,927,934 | 5/1990 | Abou-Gharbia et al. ..... 546/152 |
| 4,940,585 | 7/1990 | Hapworth et al. ........... 424/464 |
| 4,943,428 | 7/1990 | Lucot et al. .................. 424/10 |
| 4,963,557 | 10/1990 | Badger et al. ................ 514/278 |
| 5,015,646 | 5/1991 | Simms .......................... 514/253 |
| 5,032,578 | 7/1991 | Horovitz ....................... 514/19 |
| 5,053,508 | 10/1991 | Schiehser et al. ............ 544/357 |
| 5,096,908 | 3/1992 | Gidda et al. .................. 514/307 |
| 5,098,889 | 3/1992 | Costall et al. ................ 514/19 |
| 5,114,947 | 5/1992 | Imondi ......................... 514/282 |
| 5,134,140 | 7/1992 | Stack ............................. 514/212 |
| 5,162,322 | 11/1992 | Taylor, Jr. et al. ............ 514/252 |
| 5,167,616 | 12/1992 | Haak et al. ................... 604/20 |
| 5,169,638 | 12/1992 | Dennis et al. ................ 424/457 |
| 5,183,819 | 2/1993 | Abou-Gharbia et al. ..... 514/255 |
| 5,185,329 | 2/1993 | Gawin et al. ................. 514/159 |
| 5,187,277 | 2/1993 | Komissarov et al. ........ 544/362 |
| 5,244,902 | 9/1993 | Sharpe et al. ................ 514/278 |
| 5,290,783 | 3/1994 | Sharpe et al. ................ 514/278 |

OTHER PUBLICATIONS

Arndt, K.Z., et al., "The Pharmacology of Topical Therapy," Dermatology in General Medicine, Ch. 211, 2532–40, T.B. Fitzpatrick, A.Z. Eisen,K. Wolff, I.M.

Freedberg and K.F. Austen, eds., 3d ed., McGraw Hill, Inc., New York (1987).

Blozovski and Sivadjian, "The Action of Serotonin, Reserpine and Other Pharmacological Agents on Sudoral Secretion", Chemical Abstracts, vol. 54, 21504 (1960).

Caccia, S., et al., "Disposition and Metabolism of Buspirone and its Metabolite 1-(2-Pyrimidinyl)-piperazine in the Rat," Xenobiotica, vol. 13, No. 3, pp. 147–153 (1983).

Coffman, J.D., "The Attenuation by Reserpine or Guanethidine of the Cutaneous Vasoconstriction caused by Tobacco smoking," Amer. Heart J., vol. 74, No. 2, pp. 229–234 (1967).

Dostal, G. and Gamelli, R.L., "The Differential Effect of Corticosteroids on Wound Disruption Strength in Mice," Arch. Surg., vol. 125, pp. 636–640 (1990).

Eison, A.S., Temple, D.L., "Buspirone: Review of its Pharmacology and Current Perspectives on its Mechanism of Action," Am. J. Med., vol. 80, pp. 1–51 (1986).

Fishel, R., et al., "Cyclosporin A Impairs Wound Healing In Rats," J. Surg. Research vol. 34, pp. 572–575 (1983).

Galli and Hammel, "Unequivocal Delayed Hypersensitivity in Mast Cell–Deficient and Beige Mice", Science, vol. 226, 710–713 (1984).

Goa, K.L., and Ward, A., "Buspirone: A Preliminary Review of its Pharmacological Properties and Therapeutic Efficacy as an Anxiolytic," Drugs, vol. 32, pp. 114–129 (1986).

Goldberg, L., and Finnerty, R., "Comparative Efficacy of Buspirone and Diazepam in the Treatment of Anxiety," Am. J. Psychiatry, vol. 136, No. 9, pp. 1184–1187 (1979).

Hellstrand, K., and Hermodsson, m S., "Role of Serotonin in the Cell Regulation of Human Natural Killer Cell Cytotoxicity," J. Immunology, vol. 139, No. 3, pp. 869–875 (1987).

Jann, M.W., "Buspirone: An Update on a Unique Anziolytic Agent," Pharmacotherapy, vol. 8, No. 1, pp. 100–116 (1988).

Jun, D.D., et al., J. Invest. Dermatol., vol. 90, p. 311 (1988).

Kligman, A.M., "The Comparative Histopathology of Male–Pattern Baldness and Senescent Baldness," Clinics in Dermatology, vol. 6, No. 4, pp. 108–118 (1988).

Metys, J., et al., "Inhibition of Passive cutaneous Anaphalaxis By Several Histamine ($H_1$) and Serotonin Antagonists in the Rat," Agents and Actions, vol. 23, pp. 331–333 (1988).

Milburn, C.M., and Peroutka, S.J., J. Neurochem., vol. 52, pp. 1787–1792 (1989).

New, J.S., et al., "Buspirone Analogues, 2, Structure—Activity Relationships of Aromatic Imide Derivatives," J. Med. Chem, vol. 29, pp. 1476–1482 (1986).

Schroeder and Christophers, "Transient Absence of C5a–Specific Neutrophil Function in Inflammatory Disorders of the Skin", The Journal of Investigative Dermatology, vol. 85, 194–98 (1985).

Seppala, T., et al., "Effects of Alcohol on Buspirone and Lorazepam Actions," Clin. Pharmacol. Ther., pp. 201–207 (1982).

Singh, G., Corticosteroids in Corneal Endothelial Wound Healing, Annals of Opthalmology, vol. 17, No. 1 (1985).

Taylor, D.P., "Buspirone, a New Approach to the Treatment of Anxiety," Faseb J., vol. 2, pp. 2445–2452 (1988).

Tucker, "Inflammation in Acne Vulgaris: Leukocyte Attraction and Cytotoxicity by Comedonal Material", The Journal of Investigative Dermatology, vol. 74, 21–25 (1980).

vanWauwe, P., and Goossens, J.G., "Arabinogalactan—and Dextran–induced Ear Inflammation in Mice: Differential Inhibition by H1–antihisamines, 5–HT–Serotonin Antagonists and Lipoxygenase Blockers," Agents and Actions, vol. 28, pp. 78–82 (1989).

Wershil et al, "Mast Cell–Dependent Amplification of an Immunologically Nonspecific Inflammatory Response", Journal of Immunology, vol. 140, 2356–60 (1988).

Wong, D.T.W., et al., "Human Eosinophils Express Transforming Growth Factor–Alpha," J. Exp. Chem., vol. 172, pp. 673–681 (1990).

Wong, D.T.W., et al., "Eosinophils From Patients with Blood Eosinophilia Express Transforming Growth Factor $\beta1$", Blood, vol. 78, pp. 2702–2707 (1991).

Wu, et al., J. Med. Chem., vol. 15, p. 477 (1972).

TOPICAL APPLICATION OF BUSPIRONE FOR TREATMENT OF PATHOLOGICAL CONDITIONS ASSOCIATED WITH IMMUNE RESPONSES

BACKGROUND OF THE INVENTION

This invention is in the area of the topical treatment of cutaneous, ocular, and mucosal hypersensitivity and hyperproliferative conditions induced by or associated with an immune response, that includes the application of an effective amount of buspirone or a buspirone derivative, or a pharmaceutically acceptable salt thereof, optionally in a pharmaceutically acceptable carrier.

The immune system specifically recognizes and selectively eliminates foreign invaders, or other antigenic agents, by a process known as the immune response. The immune response has three major characteristics: it responds adaptively to foreign invaders, it exhibits strong specificity, and it displays a long-term memory of earlier contacts with specific foreign pathogens or antigens. The immune response involves the production of antibodies and/or the destruction of antigenic cells by T lymphocytes; both the antibodies and the T lymphocytes are highly specific for the antigen or hapten.

The immune response can provide great benefit to the host when directed against an infectious organism. As an example, an important component of current public health practices is the use of vaccines to elicit immune responses against infectious organisms that cause severe illness and death. However, when directed against agents that are relatively innocuous, such as pollen, animal dander, and certain plant resins, the cells, antibodies, and mediators which represent the effector components of the immune response can cause damage to the host's tissues that is out of proportion to any threat to health posed by the antigenic agent that first elicited the response.

For example, cutaneous contact hypersensitivity responses are complex expressions of cellular immunity characterized by antigen-dependent changes in lymphocyte traffic, the recruitment of circulating leukocytes to the site of antigen challenge (leukocyte infiltration) and alterations in vascular permeability and blood flow resulting in tissue swelling (edema). In humans and companion animals, cutaneous contact hypersensitivity responses can occur on exposure to certain plant resins, such as those of poison ivy, and other commonly encountered agents in the environment. In individuals sensitized to such commonly encountered agents, a severe contact reaction can result upon exposure, with significant associated morbidity. Severe or repeated contact hypersensitivity reactions can be followed by significant chronic changes, such as scarring of affected tissues, itchiness, swelling, scaling and oozing of tissue fluid through the skin surface. This pathology may predispose the patient to bacterial superinfection. In the eye, chronic immune responses can lead to diminished vision or actual blindness. In the lung, chronic immune responses, such as chronic allergic asthma, can result in serious chronic lung disease.

Cutaneous contact hypersensitivity and asthma are just two examples of immune responses that can be associated with significant morbidity. Others include atopic dermatitis, eczema, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, lichen planus, asthma, allergic asthma, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Similarly, psoriasis, a common cutaneous disease associated with a hyperproliferating epidermis, also has a leukocyte infiltration component. Immunologically mediated leukocyte infiltration also occurs at sites other than the skin, such as in the airways in asthma and in the tear producing gland of the eye in keratoconjunctivitis sicca.

It is now believed that leukocytes and other cells found in the normal and abnormal skin, eye, or mucosal membranes secrete a variety of cytokines. During immunological responses affecting these sites, cytokines are important in recruiting additional leukocytes into these tissues, in promoting epithelial hyperproliferation, and in inducing other chronic changes such as scarring. For example, eosinophils, a type of granulocyte found in many pathological immune responses including atopic dermatitis and asthma, can produce the cytokine TGF-$\alpha$ (Wong D. T. W., Weller P. F., Galli, S. J., Elovic A., Rand, T. H., Gallagher, G. T., Chiang, T., Chou, M. Y., Matossian, K., McBride, J., Todd, R. Human eosinophils express transforming growth factor-alpha. *J. Exp. Med.* 1990; 172:673–81), which promotes epithelial hyperproliferation, and TGF-$\beta$ (Wong, D. T. W., Elovic, A., Matossian, K., Nagura, N., McBride, J., Chou, M. Y., Gordon, J. R., Rand, T. H., Galli, S. J., Weller, P. F. Eosinophils from patients with blood eosinophilia express transforming growth factor $\beta$1. *Blood* 1991; 78:2702–2707), which promotes fibrosis.

In addition to disorders that clearly represent pathological consequences of immune responses, immune responses are thought to contribute to many other pathological conditions, including Crohn's disease and ulcerative colitis of the gastrointestinal tract, psoriasis, alopecia areata and others. While the cause of most of these disorders is unclear, it is thought that exogenous agents yet to be defined or components of the host's own tissues (in the case of autoimmune disorders) may provoke an immune response that is responsible for the infiltration of lymphocytes, monocytes, and granulocytes observed in these conditions. It is also believed that the infiltrating cells significantly contribute to the tissue pathology associated with these disorders, through the production of cytokines as well as by other mechanisms.

The need to control the wide variety of pathological responses with immunological components which result in cutaneous, ocular, or mucosal hypersensitivity reactions, hyperproliferation, and scarring has led to a search for therapeutic agents that are both safe and effective.

Because of the importance of leukocytes and their products in the development of pathology associated with immune responses, many approaches to treating these conditions are focused on inhibiting the immune responses and leukocyte infiltration contributing to these disorders. Several substances are known to be able to inhibit the immune responses contributing to cutaneous leukocyte responses or hyperproliferative responses. Corticosteroids, when administered systemically, are effective in this regard but are associated with significant and potentially dangerous side effects. Topically applied corticosteroids have some efficacy in treating these conditions, but are only partially effective in many instances and have their own significant side effects, including atrophy of tissue, formation of telangiectasia, blanching, and a myriad of systemic effects if significantly absorbed. Other agents with partial utility for treating some of the above conditions include psoralen plus ultraviolet A (PUVA), cyclosporin A, or azathioprine, but the risk-to-benefit ratios for these agents is unfavorable for most of the conditions described above.

As a result, there is a significant and very long-standing need to identify new agents with favorable benefit to risk ratios that can be applied topically to prevent or suppress (i.e. "treat") immune responses contributing to cutaneous, ocular, or mucosal hypersensitivity reactions, hyperproliferation and scarring. Optimally, such agents should be effective when applied locally, and systemic absorption should not result in blood levels high enough to cause significant systemic toxicity or other adverse side effects. Not only does local administration place the agent in closest contact with the site needing treatment, but it also diminishes the possibility that such treatment will suppress beneficial immune responses which may occur at other, more distant, sites.

In contrast to the immune response, an inflammatory response is a pathologic condition that can occur in response to immunologically non-specific injury, either from physical (such as trauma), chemical, or biologic agents. An inflammatory response is characterized by increased blood flow and redness in the inflamed area, increased capillary permeability and edema, and recruitment of immunologically non-specific white blood cells, especially neutrophils, that remove injurious material and promote repair. Unlike immune responses, inflammatory responses do not respond adaptively to the inciting stimulus, do not show specificity and do not exhibit long term memory. Cellular products of lymphocytes may contribute to or induce an inflammatory response. However, because of the differences in mechanisms, a compound can function as an anti-inflammatory agent without having immunosuppressive properties. Phenylbutazone, indomethacin, aspirin, ibuprofen, and acetaminophen are examples of anti-inflammatory compounds which have no significant immunosuppressive activity, as demonstrated by their lack of a significant effect on immunologically mediated responses, such as contact hypersensitivity.

PCT International Publication No. WO 91/02527 discloses a method and composition to treat cutaneous, mucosal, or ocular hypersensitivity that includes administering an effective amount of reserpine, spiperone, or other serotonin antagonist.

Buspirone (8-[4-[4-(2-pyrimidinyl)-1-piperazinyl]butyl]-8-azaspiro[4.5][decane-7.9-dione) is a neuroleptic agent with known central nervous system (CNS) dopamine and serotonin (5-HT) receptor antagonist properties.

It is an object of the present invention to present a method for the topical treatment of cutaneous, mucosal and ocular pathology associated with immune responses.

It is yet another object of the present invention to present a method for the topical treatment of cutaneous, mucosal, or ocular hypersensitivity and epithelial hyperproliferation.

It is yet another object of the invention to present a method for the topical treatment of cutaneous, mucosal or ocular scarring.

SUMMARY OF THE INVENTION

A method for the treatment of a cutaneous, ocular, or mucosal condition in a human or other mammal resulting from pathology associated with an immune response is provided that includes topical application of an effective amount of buspirone or a buspirone derivative or its pharmaceutically acceptable salt, in a pharmaceutically-acceptable diluent or carrier for topical application.

Buspirone exhibits a strong immunosuppressive activity when applied topically. The parent buspirone is used herein as the model of an active topical immunosuppressant. Buspirone derivatives are measured against this model, and are considered to be immunosuppressants if they suppress the ear swelling associated with an experimental contact hypersensitivity response by at least 40% at 2 hours after specific antigen challenge.

In the preferred method of administration, the active compounds are administered topically in a suitable carrier in an amount sufficient to effectively immunosuppress the patient at the site of application. Because the application is topical, i.e., local, immunosuppression is achieved without producing significant systemic effects, most notably, the significant neuroleptic effect that is associated with the systemic administration of buspirone.

Buspirone and its active derivatives are administered as general immunosuppressive agents. The compounds may be useful as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds may also be effective to treat an aqueous-deficient dry eye state (such as immune mediated keratoconjunctivitis) in a patient suffering therefrom, by administering the compound topically to the eye.

BRIEF DESCRIPTION OF THE DRAWINGS

As used in FIGS. 1–2 and Examples 1–2 only, the term "buspirone" refers to buspirone HCl.

DETAILED DESCRIPTION OF THE INVENTION DEFINITIONS

Figure 1:
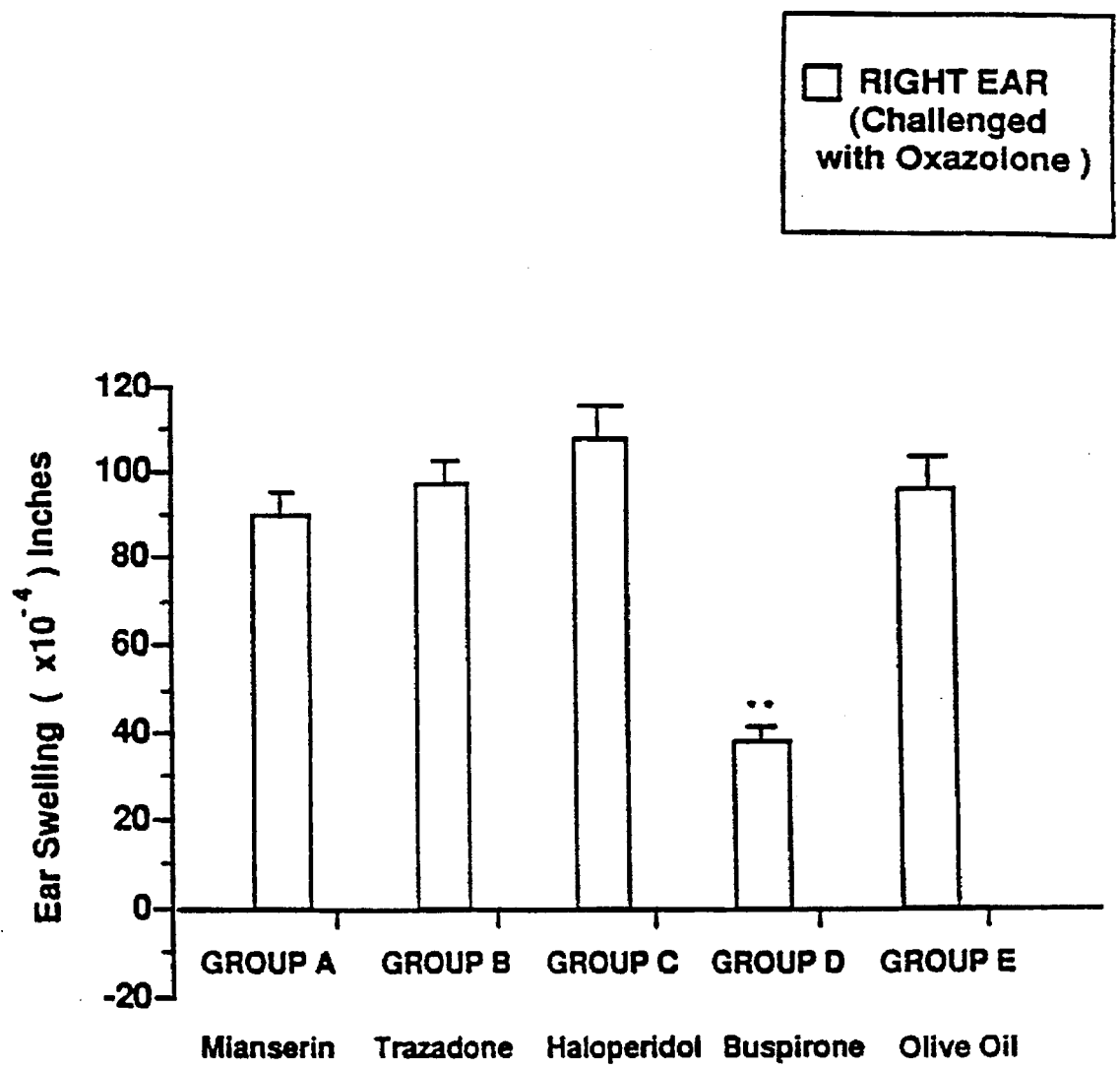
FIG. 1—Comparative effects of 50 mg/kg subcutaneous administration of mianserin HCl (Group A), trazadone HCl (Group B), haloperidol (Group C), buspirone HCl (Group D), and vehicle (Group E) on the tissue swelling associated with oxazolone-induced cutaneous contact hypersensitivity reactions. Buspirone, the other agents, or vehicle alone were administered to BALB/c mice 1 hour after right ears only were challenge for contact hypersensitivity. The change in ear thickness (post-challenged value minus baseline pre-challenge value) was measured 24 hours after oxazolone challenge. The data are presented as the mean±SEM. The reduction in ear swelling observed with buspirone was significant when compared to the reactions observed in the challenged right ears of the control, vehicle (Group E, olive oil) treated animals (**=p<0.01), whereas haloperidol, trazadone and mianserin did not significantly suppress the tissue swelling associated with contact hypersensitivity.
Figure 2:
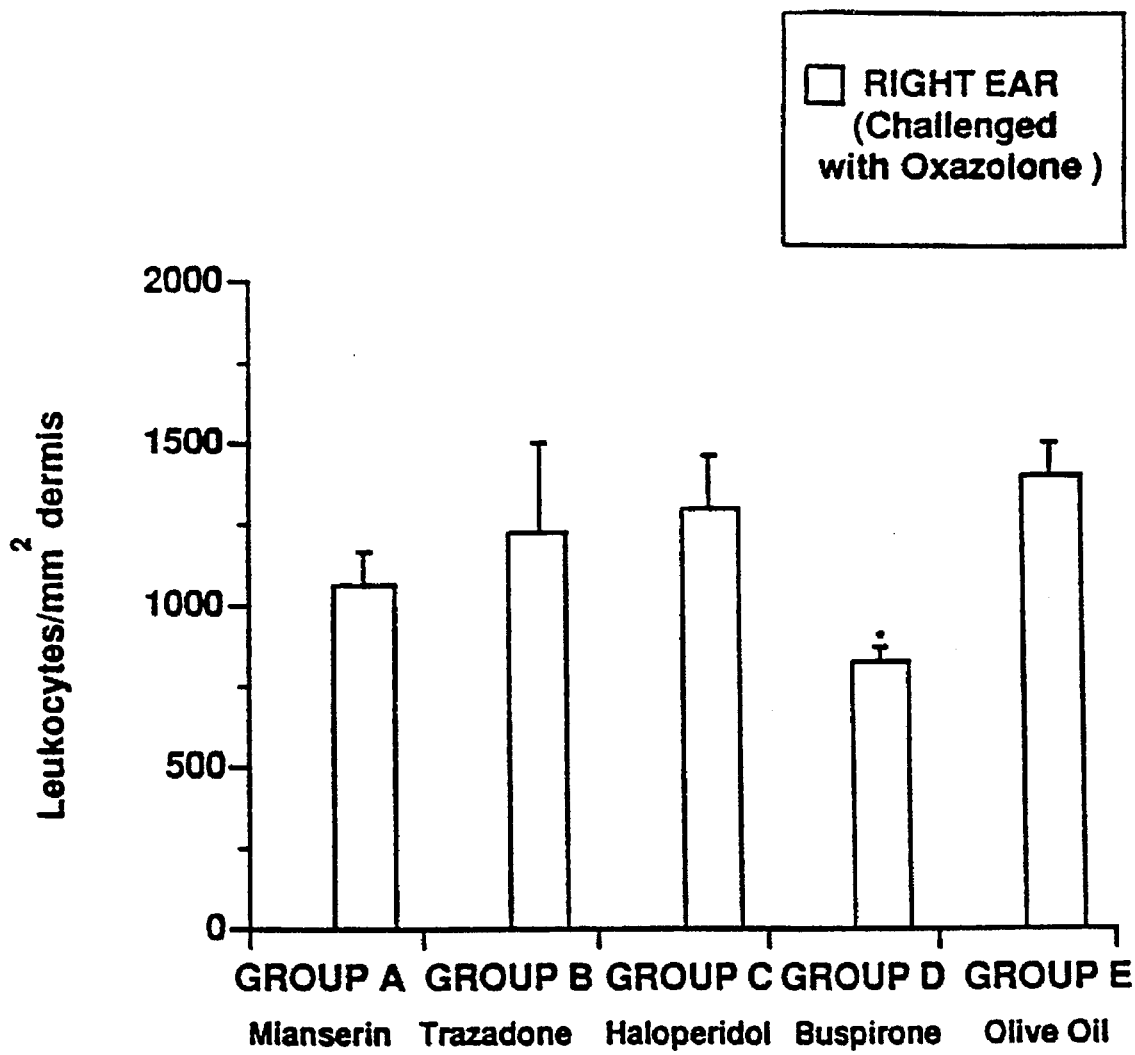
FIG. 2—Comparative effects of subcutaneous administration of 50 mg/kg mianserin HCl (Group A), trazadone HCl (Group B), haloperidol (Group C), buspirone HCl (Group D), and systemic vehicle (Group E) on leukocyte infiltration associated with 24-hour contact hypersensitivity reactions. These data (mean±SEM) are derived from the same mice whose ear thickness values are shown in FIG. 3. The reduction in leukocyte infiltration observed in the right (oxazolone-challenged) ears of animals treated with buspirone was significant when compared to the reactions observed in animals treated with vehicle alone (*=p<0.05), while haloperidol, trazadone and mianserin did not significantly suppress the leukocyte infiltration associated with contact hypersensitivity.

The term alkyl, as used herein, unless otherwise specified, refers to a saturated straight, branched, or cyclic hydrocarbon of $C_1$ to $C_{20}$, including methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term aryl, as used herein, and unless otherwise specified, refers to phenyl or substituted phenyl, wherein the substituent is independently halo, alkyl, or oxy(alkyl) (for example, methoxy, ethoxy, etc.), and wherein the aryl can have up to three substituents.

The term heterocycle refers to a cyclic moiety that has O, S, or N in the aromatic ring, including but not limited to, pyrryl, furyl, pyridyl, thiophene, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbozolyl, and isoxazolyl and the like, optionally substituted with halo (Cl, Br, I, or F), alkyl, oxyalkyl, aryl or oxyaryl.

The term aralkyl refers to an aryl group with an alkyl substituent.

The term alkaryl refers to an alkyl group that has an aryl substituent.

The term alkene, as referred to herein, and unless otherwise specified, refers to an alkene group of $C_2$ to $C_{10}$, and specifically includes vinyl, and allyl.

As used herein, the term "buspirone" refers to the compound (8-[4-[4-(2-pyrimidinyl)-1-piperazinyl]butyl]-8-azaspiro-[decane-7,9-dione).

The term "buspirone derivative" as used herein refers to a compound that exhibits an immunosuppressive effect when provided topically, as measured using the assay set out in Example 1, i.e., it suppresses the ear swelling associated with an experimental contact hypersensitivity response by at least 40% at 24 hours after specific antigen challenge, or as evaluated in vivo in humans by the agent's ability to inhibit contact hypersensitivity responses to patch test allergens in patients hypersensitive to a given allergen, using procedures generally accepted by those of skill in the art, and wherein the derivative has the formula:

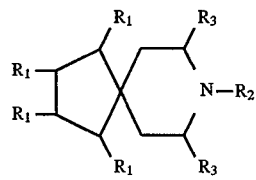

wherein:

$R_1$=H; halo (chloro, bromo, fluoro, or iodo); alkyl, specifically including $CH_3$—, cyclohexyl, $(CH_3)_2CH$—, $CH_3(CH_2)_3$—, $(CH_3)CHCH_2$—, $CH_3CH_2CH(CH_3)$—, $(CH_3)_3C$—, and —$CH_3(CH_2)_p$; Y—$CH_2(CH_2)_n$—; oxyalkyl; or aryl, specifically including $C_6H_5$—, (2, 3, or 4)—$(OCH_3)C_6H_4$— and (2, 3, or 4)—$(CH_3)C_6H_4$—; 2—X—$C_6H_4$—, 3—X—$C_6H_4$—, or 4—X—$C_6H_4$—; oxyaryl; or alkaryl;

$R_2$=H, $C_6H_5CH(CH_2CH_3)CH_2$—, $C_6H_5CH(CH_3)$-$(CH_2)_2$—, $C_6H_5CH_2CH(CH_3)CH_2$—, $C_6H_5CH_2CH_2CH(CH_3)$—, $C_6H_5CH(CH_3)(CH_2)_3$—, (2, 3, or 4)-(alkyl)—$C_6H_4CH(CH_3)(CH_2)_3$—, (2, 3, or 4)-(alkyloxy)—$C_6H_4CH(CH_3)(CH_2)_3$, (2, 3, or 4)—X—$C_6H_4$-alkyl, specifically including (2, 3, or 4)—X—$C_6H_4CH(CH_2CH_3)CH_2$—, (2, 3, or 4)—X—$C_6H_4CH(CH_3)(CH_2)$—4—X—$C_6H_4CH(CH_3)(CH_2)_2$—, and 4—X—$C_6H_4$—$CH(CH_3)(CH_2)_3$—; $C_6H_5CH$ $(OCH_3)(CH_2)_2$—,

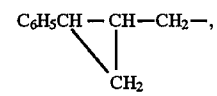

$C_6H_5CO(CH_2)_3$—, $C_6H_5CO(CH_2)_4$—, (2, 3, or 4)-(alkyl)—$C_6H_4CO(CH_2)_3$—, (2, 3, or 4)-(alkyl-oxy)—$C_6H_4CO(CH_2)_3$—, (2, 3, or 4)—X—$C_6H_4CO$ $(CH_2)_n$—, 2-thienyl—CO—$(CH_2)_3$—, -alkyl-piperazinyl-aryl; -alkyl-$C_{3-8}$cycloalkyl-aryl; -alkyl-piperazinyl-heterocycle; -alkyl-$C_{3-8}$cycloalkyl-heterocycle; -alkyl-$C_{3-8}$cycloalkyl-$Ar_1$; -alkyl-piperazinyl-$Ar_1$; -alkenyl-piperazinyl-aryl; -alkenyl-$C_{3-8}$cycloalkyl-aryl; -alkyl-aryl-heterocycle; -alkyl-heterocycle-aryl; -alkenyl-$C_{3-8}$cycloalkyl-$Ar_1$; -alkenyl-piperazinyl-heterocycle; -alkenyl-$C_{3-8}$cycloalkyl-heterocycle; -alkenyl-piperazinyl-$Ar_1$;

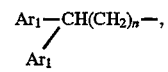

(2, 3, or 4)—X—$C_6H_4C(CH_3)CH(CH_2)_2$—, where the conformation about the double bond is cis or trans, (2, 3, or 4)—X—$C_6H_4C(CH_3)CHCH_2$—, where the conformation about the double bond is cis or trans, (2, 3, or 4)—X—$C_6H_4COCH=CHCH_2$—, Y—$CH_2$ $(CH_2)_n$—, $Ar_1$—$(CH_2)_n$—, $C_1$ to $C_{20}$ alkyl, X—$(CH_2)_nCO$—, or X—$(CH_2)_n$—;

$R_3$ =O, =NH, =S, chloro, bromo, iodo, fluoro, alkyl, or aryl;

n=1 to 6;

p=1 to 20;

x=is independently F, Cl, Br, I, $OCH_3$, $SO_3$, $NH_2$, H, —OH, —COOH, —COOR, —$SO_3H$, —CN, —$NHSO_3H$, —$NO_2$, or —$SO_2NH_2$;

y=H, F, Cl, Br, I, —$SO_3$, —$PO_4^=$, —OH, —SH, —$SCH_3$, —$CH_3SO_2$, —$NH_2$, or —$CO_2$; and $Ar_1$=independently, aryl, (2, 3, or 4—X—$C_6H_4$—), (2, 3, or 4)—$(CH_2X)C_6H_4$—, (2, 3, or 4)—$(CX_3)C_6H_4$—, (2, 3, or 4)—$(CHX_2)C_6H_4$—, 2-thienyl, or (2, 3, or 4)—X—$C_6H_4CH_2$—;

or its pharmaceutically acceptable salt, including any quaternary salt known to those in the art, and specifically including the quaternary ammonium salt of the formula —$NR^+Z^-$, wherein R is alkyl (and in particular methyl or ethyl) or benzyl, and Z is a counteranion, including chloride, bromide, iodide, —O-alkyl, toluenesulfonate, methylsulfonate, sulfonate, sulfate, phosphate, or carboxylate (such as benzoate, succinate, acetate, glycolate, propionate, maleate, malate, citrate, tartrate, ascorbate, benzoate, cinnamoate, mandeloate, benzyloate, and diphenylacetate).

I. Structure and Synthesis of Buspirone Derivatives

The parent buspirone is 8-[4-[4-(2-pyrimidinyl)-1-piperazinyl]butyl]-8-azaspiro-[4.5]decane-7,9-dione, which has the structure illustrated below.

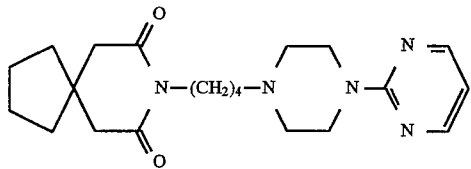

As demonstrated in Example 1, the parent buspirone has significant immunosuppressive activity when applied topically. The potential utility of any one of the above-described buspirone derivatives to act as an immunosuppressant can be conveniently determined by synthesizing the compound and testing it in the biological assay described in Example 1.

Those derivatives of buspirone which are particularly useful in the method of the invention are those which have decreased or no affinities for dopamine and/or serotonin receptors, but which retain immunosuppressive properties.

Methods of synthesis of buspirone or its derivatives are disclosed in, or can be easily adapted by one of ordinary skill in organic synthesis from procedures disclosed in Wu, et al., *J. Med. Chem.* 15, 477 (1972), Ger. Patent No. 2,057,845, and U.S. Pat. No. 3,717,634. See also J. Clin. Psychiat. 43, 1–116 (1982).

II. Therapeutic Compositions

Mammals, and specifically humans, suffering from pathological cutaneous, ocular, or mucosal immune responses can be treated by topical administration to the patient of an effective amount of the buspirone derivative or its salt, optionally in combination with a pharmaceutically acceptable carrier or diluent.

The active compound is administered topically in an effective dosage range to cause immunosuppression of the target pathological immune response. The active compound is included in the pharmaceutically acceptable carrier or diluent in an amount sufficient to deliver to a patient a therapeutic amount of the buspirone derivative in vivo in the absence of serious toxic effects. In general, local immunosuppression can be achieved by topically administering lower doses of buspirone derivatives than would be required if the agents were administered systemically.

The range of daily dosage for the herein-identified conditions is from 0.01 grams to 60 grams of topically administered pharmaceutical composition containing 0.01% to 10% by weight buspirone.

Buspirone or its derivative is administered for a sufficient time period to alleviate the undesired symptoms and the clinical signs associated with the condition being treated. The concentration of active compound in the drug composition will depend on absorption, inactivation, and other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

Buspirone or its derivative can be mixed with other active materials which do not impair the desired action, or with materials that supplement the desired action, such as antibiotics, antifungals, anti-inflammatories, antivirals, or other immunosuppressive agents.

Solutions or suspensions for topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide.

Suitable vehicles or carriers for topical application are known, and include lotions, suspensions, ointments, creams, gels, tinctures, sprays, powders, pastes, slow-release transdermal patches, aerosols for asthma, suppositories for application to rectal, vaginal, nasal or oral mucosa, mouthwashes, or swish and spit preparations.

Thickening agents, emollients, and stabilizers can be used to prepare topical compositions. Examples of thickening agents include petrolatum, beeswax, xanthan gum, or polyethylene glycol, humectants such as sorbitol, emollients such as mineral oil, lanolin and its derivatives, or squalene. A number of solutions and ointments are commercially available, especially for ophthalmic and dermatologic applications.

Natural or artificial flavorings or sweeteners can be added to enhance the taste of topical preparations applied for local effect to mucosal surfaces. Inert dyes or colors can be added, particularly in the case of preparations designed for application to oral mucosal surfaces.

Buspirone or its derivative can be applied in a time release formulation via patches or by slow release polymers. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. The materials can also be obtained commercially from Alza Corporation and Nova Pharmaceuticals, Inc.

Buspirone or its derivatives can be provided in the form of pharmaceutically-acceptable salts. As used herein, the term "pharmaceutically-acceptable salts or complexes" refers to salts or complexes that retain the desired biological activity of the parent compound and exhibit minimal, if any, undesired toxicological effects. Examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with polyvalent metal cations such as zinc, calcium, bismuth, barium, magnesium, aluminum, copper, cobalt, nickel, cadmium, and the like, or with an organic cation formed from N,N-dibenzylethylene-diamine or ethylenediamine; or (c) combinations of (a) and (b); e.g., a zinc tannate salt or the like.

The buspirone derivatives can be modified in order to enhance their usefulness as pharmaceutical compositions. For example, it is well know in the art that various modifications of the active molecule, such as alteration of charge, can affect water and lipid solubility and thus alter the potential for percutaneous absorption. The vehicle, or carrier, can also be modified to enhance cutaneous absorption, enhance the reservoir effect, and minimize potential irritancy or neuropharmacological effects of the composition. See, in general, Arndt, K. A., P. V. Mendenhall, "The Pharmacology of Topical Therapy", *Dermatology in General Medicine*, 1987; T. B. Fitzpatrick, A. Z. Eisen, K. Wolff, I. M. Freedberg and K. F. Austen, eds., 3d ed., McGraw Hill, Inc., New York, pp. 2532–2540.

III. Immunosuppressant Activity of Buspirone Derivatives

Buspirone and buspirone derivatives are capable of suppressing the immune response in humans and other mammals on topical application. As such, the compounds, or therapeutic compositions thereof, may be useful for the treatment of a myriad of immunological disorders.

The ability of buspirone to influence the tissue swelling associated with contact hypersensitivity reactions in mice was evaluated as described in detail in Example 1. The parent buspirone compound was used for the procedure in Example 1 as a model of an active immunosuppressant. Buspirone derivatives can be measured against this model, and are considered active if they suppress the swelling response by at least 40% 24 hours after specific antigen challenge.

Mice treated topically with buspirone, unlike those treated systemically, exhibited no significant drowsiness.

Buspirone expresses both serotonin and dopamine receptor antagonist activity. However, unlike buspirone, it was discovered that the chemically unrelated serotonin antagonists, trazadone and mianserin, and the dopamine receptor antagonist, haloperidol, were not effective in suppressing contact hypersensitivity. On the basis of this, it appears that the mechanism of action of buspirone on the immune response is independent of its serotonin or dopamine receptor blocking properties.

EXAMPLE 1

Inhibition of Induced Contact Hypersensitivity.

Six-to-8-week-old female C57BL/6J or BALB/c mice were obtained from the Jackson Laboratory, Bar Harbor, Maine or from Charles River Laboratories, Kingston Facility, Stoneridge, N.Y., respectively.

Buspirone, mianserin, trazadone, haloperidol and oxazolone were purchased from the Sigma Chemical Co. (St. Louis, Mo.).

Oxazolone-Induced Contact Hypersensitivity Sensitization—Sensitization and challenge for contact hypersensitivity were performed as follows. The abdomens of the mice were shaved with electric clippers, 50 µl of a 4% (w/w) solution of oxazolone in 4:1 (v:v) acetone:olive oil were applied to the shaved abdomen, and 5 µl of the same solution were applied to each hind footpad. Five to eight days later, the mice were challenged for contact hypersensitivity by applying 10 µl of a 0.5% (w:w) solution of oxazolone in 4:1 (v:v) acetone:olive oil to both the inner and outer surface of the right ear of each mouse (in the case of mice treated systemically with buspirone) or to both ears (in the case of mice treated topically with buspirone).

Systemic Buspirone Treatment—One hour of after the application of oxazolone for elicitation of contact hypersensitivity, mice were treated subcutaneously with buspirone 500 or 50 mg/kg body weight) in 0.1 ml of carrier (Cremophor EL, BASF, Parsippany, N.J.), or with 0.1 ml of carrier alone. In a separate experiment, mice were treated in a similar fashion with 50 mg/kg body weight of trazadone, mianserin, haloperidol, or buspirone in 1 ml olive oil or with olive oil alone.

Topical Buspirone Treatment For these experiments, both ears of each mouse were challenged for elicitation of contact hypersensitivity by the application of oxazolone (as appropriate) to both surfaces of both ears. Two hours before, or twenty-four hours after application of hapten, the right ears of some mice were treated with buspirone in vehicle, applied epicutaneously to both surfaces. The right ears of control mice were similarly treated, but with vehicle alone. In the case of experiments designed to evaluate the topical effect of buspirone on the sensitization phase, only the right ear is challenged (see FIGS. 9 and 10).

Evaluation of Ear Swelling Response—immediately before and 24 or 48 hours after application of oxazolone, ear thicknesses were determined with an engineer's micrometer. The increment (delta) in ear thickness (ear swelling) was calculated as the 24- or 48-hour value minus the baseline (pre-challenge) value and expressed in units of $10^{-4}$ inches. Mice were killed by cervical dislocation after the measurement of 24-hour ear thickness was obtained, and the ears were processed for histologic examination.

Quantification of Leukocyte Infiltration—Both ears of each mouse were fixed in 4.0% buffered formalin and then processed routinely and embedded in paraffin for preparation of 6–7 µm-thick hematoxylin and eosin-stained sections. All of the sections were coded and examined with an ocular grid at 400× under light microscopy by an observer unaware of the identity of the individual slides. The number of leukocytes/mm$^2$ of dermis was calculated by counting all of the leukocyte cells in an area of at least 0.14 mm$^2$ of dermis.

Statistical Analysis—Differences between groups were assessed by the 2-tailed Student's t test (paired for comparisons of left and right ears in the same mice, unpaired for comparisons between different groups of mice).

Effect of Systemic Buspirone Versus Other Serotonin or Dopamine Receptor Antagonists—In these experiments, systemic buspirone was compared to the serotonin receptor antagonists, trazadone or mianserin, and to the dopamine receptor antagonist, haloperidol, for their ability to inhibit cutaneous contact hypersensitivity. At a dose of 50 mg/kg, only buspirone significantly reduced cutaneous contact hypersensitivity (FIG. 1, 2).

EXAMPLE 2

Comparison of Immunosuppressant Versus Anti-Inflammatory Activity.

Mice were sensitized to oxazolone as described in Example 1. Three days later, slow release indomethacin pellets (0.05 mg, 3 week release) were implanted subcutaneously under light ether anesthesia. The dose of indomethacin delivered by these pellets has been previously shown to completely block prostaglandin synthesis in mice, by Jun, D. D., et al., *J. Invest. Dermatol.* 90:311 (1988).

Three days later, mice were challenged for contact hypersensitivity as in Example 1. When the hypersensitivity response was assessed 24 hours later, indomethacin was shown to have no significant effect on the response. A classic anti-inflammatory agent, indomethacin, does not appear to suppress the edema associated with the immunologically specific oxazolone induced contact hypersensitivity response and compared to buspirone, only weakly suppresses the leukocyte infiltration associated with the response.

EXAMPLE 3

Evaluation of Serotonin Receptor Binding Activity or Dopamine Receptor Binding Activity of Buspirone Derivatives.

Buspirone derivatives which lack serotonin receptor binding or dopamine receptor binding activity can be identified as follows. A radiolabeled ligand known to bind serotonin and/or dopamine receptors can be bound to an appropriate substrate expressing one or both of these receptors. For example, radiolabeled quipazine which is available commercially can be used as the ligand. The buspirone derivative to be tested is then incubated with the radiolabeled quipazine ligand combination. Displacement of radiolabeled ligand is positive evidence that the buspirone derivative being tested can bind serotonin and/or dopamine receptors. The amount of radiolabeled ligand which is displaced is determined by an appropriate standard curve which can also provide information concerning binding affinities. The displaced radiolabeled ligand can be quantitated using a standard scintillation counter.

A detailed description of how to perform the binding studies using $^3$H-quipazine and the example follows:

Binding studies using $^3$H-quipazine are described in detail by Milburn, C. M. and Peroutka, S. J., *J. Neurochem.* 52:1787–1792 (1989). Briefly, rat cortices are homogenized in 20 volumes of 50 mM Tris HCl buffer pH 7.7 at 25° C. and centrifuged at 49,000× g for 10 min. The pellet is resuspended in fresh buffer and incubated at 37° C. for 10 min. After the final centrifugation, the pellet is resuspended in 80 volumes of Krebs-HEPES buffer (25 mM HEPES, 118 mM NaCl, 5 mM KCl, 2.5 mM CaCl$_2$, and 1.2 mM MgCl$_2$ pH adjusted to 7.4). Tissue (10 mg of original wet weight) is added to assay tubes containing 0.8 nM [$_3$H]quipazine and displacing drug or buffer in a final volume of 1 ml. Nonspecific binding is defined using 1 micromole zacopride. After a 30 min incubation at room temperature, the tissue is rapidly filtered under vacuum through No. 32 glass fiber filters and rinsed twice with 5 ml of 50 mM Tris-HCl buffer pH 7.7. Radioactivity is quantified by liquid scintillation counting. All experiments are performed three to six times, each in triplicate. This same approach can be used with other radiolabeled ligands such as zacopride, granisetron, haloperidol, mianserin, ketanserin, 5-HT, dopamine, droperidol, or ritanserin.

Buspirone derivatives which have binding affinities for dopamine and/or serotonin receptors of one/tenth or less than the parent buspirone are considered to be potentially useful as systemic immunosuppressants if they are at least 50% as active as the parent buspirone on a weight basis in suppressing immunologically specific responses such as contact hypersensitivity.

Modifications and variations of the present invention relating to methods for the treatment of pathology associated with immune responses that includes topical administration of an effective amount of buspirone or a buspirone derivative will be obvious to those skilled in the art from the foregoing detailed description of the invention. Such modifications and variations are intended to come within the scope of the appended claims.

We claim:

1. A method for the treatment of a cutaneous, ocular, or mucosal pathology associated with an immune response in a human or other mammal that includes topical application of an effective amount of buspirone or its pharmaceutically acceptable salt, other than a quaternary salt, optionally in a pharmaceutically acceptable diluent or carrier for topical application.

2. The method of claim 1 wherein the mammal is a human.

3. The method of claim 1, wherein the pathology associated with an immune response is contact hypersensitivity.

4. The method of claim 1, wherein the carrier is a mouthwash.

5. The method of claim 1, wherein the carrier is a swish and spit solution.

6. The method of claim 1 wherein the compound in combination with an ophthalmic carrier is topically applied to the eye.

7. The method of claim 1, wherein the compound is applied cutaneously.

8. The method of claim 1, wherein the compound is applied to mucosal membranes.

9. The method of claim 1, wherein the daily dose of compound is between 0.01 and 60 grams.

10. The method of claim 1, wherein the compound is applied in a concentration between 0.01 and 10%.

11. The method of claim 1 wherein the compound is administered in a time release formulation via a patch or by slow release polymer.

12. The method of claim 1, wherein the compound is administered via a retention enema.

* * * * *